(12) United States Patent
Pai et al.

(10) Patent No.: US 12,599,697 B2
(45) Date of Patent: Apr. 14, 2026

(54) LIQUID EMBOLIC COMPOSITIONS WITH CONTROLLED RELEASE OF RADIOPAQUE AND THERAPEUTIC COMPOUNDS AND METHODS OF USING THE SAME

(71) Applicant: Blackswan Vascular, Inc., Hayward, CA (US)

(72) Inventors: Suresh S. Pai, Los Altos, CA (US); Scott R. Sershen, Foster City, CA (US); Dorna Hakimimehr, Redwood City, CA (US); Celso J. Bagaoisan, Union City, CA (US)

(73) Assignee: BlackSwan Vascular, Inc., Hayward, CA (US)

( * ) Notice: Subject to any disclaimer, the term of this patent is extended or adjusted under 35 U.S.C. 154(b) by 489 days.

(21) Appl. No.: 18/024,452

(22) PCT Filed: Sep. 2, 2021

(86) PCT No.: PCT/US2021/048907

§ 371 (c)(1),
(2) Date: Mar. 2, 2023

(87) PCT Pub. No.: WO2022/051530

PCT Pub. Date: Mar. 10, 2022

(65) Prior Publication Data

US 2023/0277719 A1 Sep. 7, 2023

Related U.S. Application Data

(60) Provisional application No. 63/074,924, filed on Sep. 4, 2020.

(51) Int. Cl.
| | |
|---|---|
| *A61K 9/50* | (2006.01) |
| *A61L 24/00* | (2006.01) |
| *A61L 24/02* | (2006.01) |

(52) U.S. Cl.
CPC ....... *A61L 24/0047* (2013.01); *A61L 24/0015* (2013.01); *A61L 24/02* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 5,667,767 | A | 9/1997 | Greff et al. |
| 5,695,480 | A | 12/1997 | Evans et al. |
| 8,940,334 | B2 | 1/2015 | Geroni et al. |
| 9,456,823 | B2 | 10/2016 | Constant et al. |
| 9,999,676 | B2 | 6/2018 | Kim et al. |
| 10,124,090 | B2 | 11/2018 | Constant et al. |
| 10,232,089 | B2 | 3/2019 | Constant et al. |
| 2018/0353522 | A1 | 12/2018 | Ghandhari et al. |
| 2019/0142946 | A1 | 5/2019 | Hohn et al. |
| 2019/0351107 | A1* | 11/2019 | Sawhney ......... A61B 17/12113 |

FOREIGN PATENT DOCUMENTS

WO WO-2020061207 A1 * 3/2020 ........... C08G 64/183

* cited by examiner

*Primary Examiner* — Susan T Tran

(74) *Attorney, Agent, or Firm* — Edward J. Baba; Christian S. Hans; Bozicevic, Field & Francis LLP

(57) ABSTRACT

The various embodiments of the subject invention included herein provide transiently radiopaque liquid embolic compositions and methods used to embolize blood vessels and/or provide controlled release of therapeutic agents when desired.

13 Claims, 7 Drawing Sheets

200

200′

200′

200′

300

301
303
302

300'

301
303
302
304    305

300'

301
303
302
304    305

300'

301
302
304    305

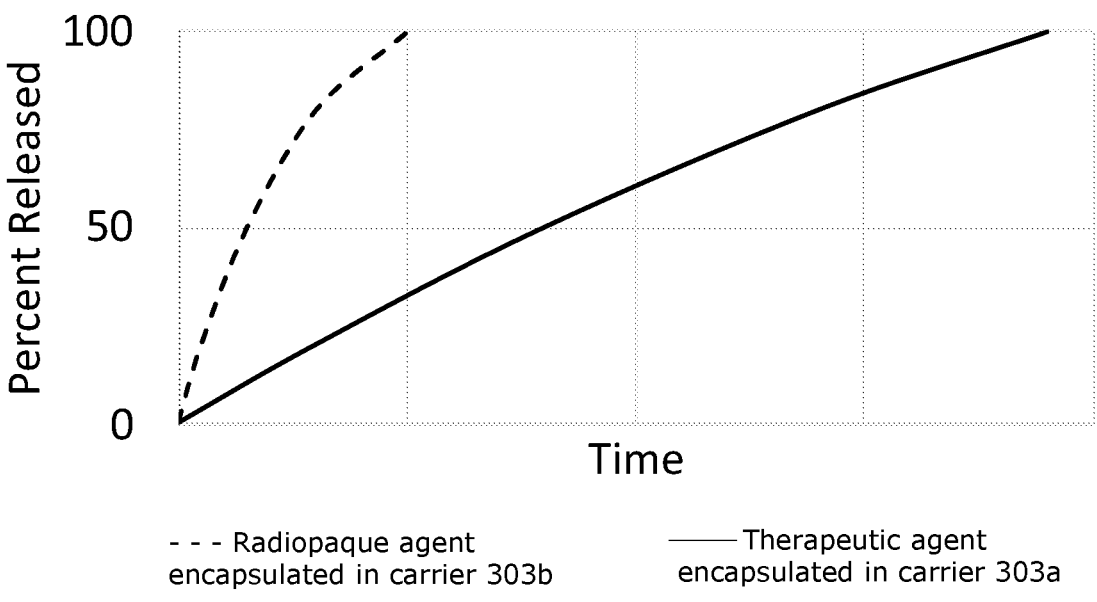
- - - Radiopaque agent
encapsulated in carrier 303b
——Therapeutic agent
encapsulated in carrier 303a
FIG. 3G
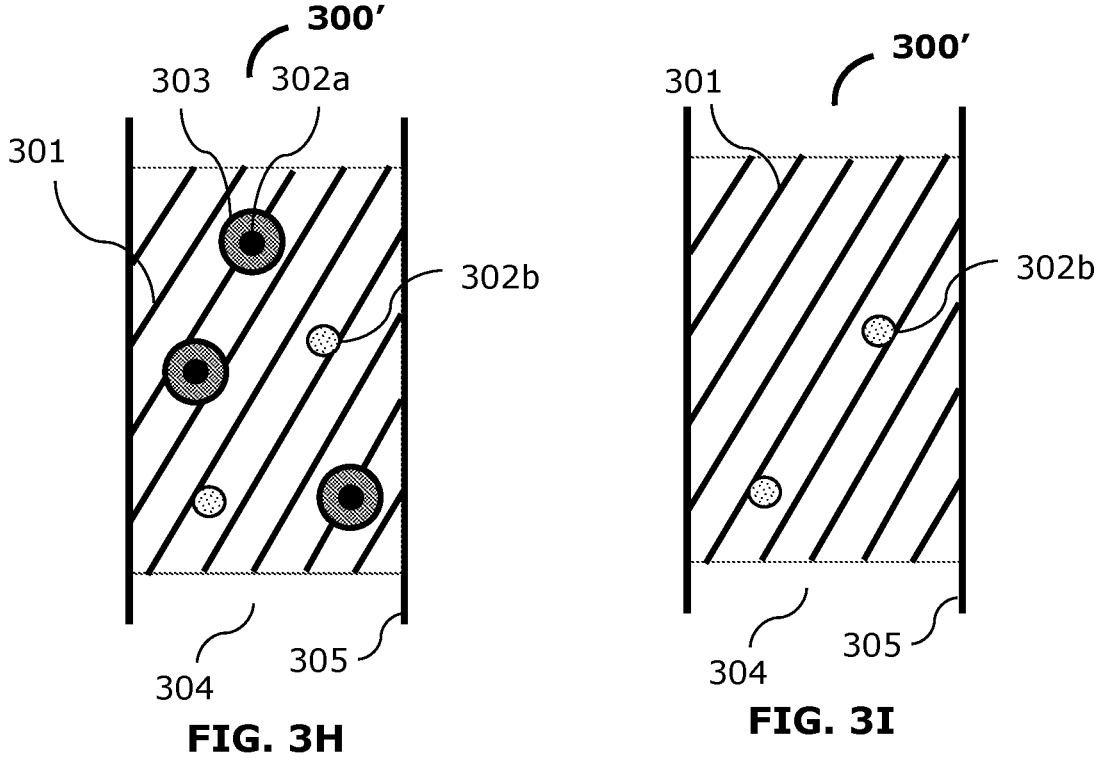
FIG. 3H
FIG. 3I

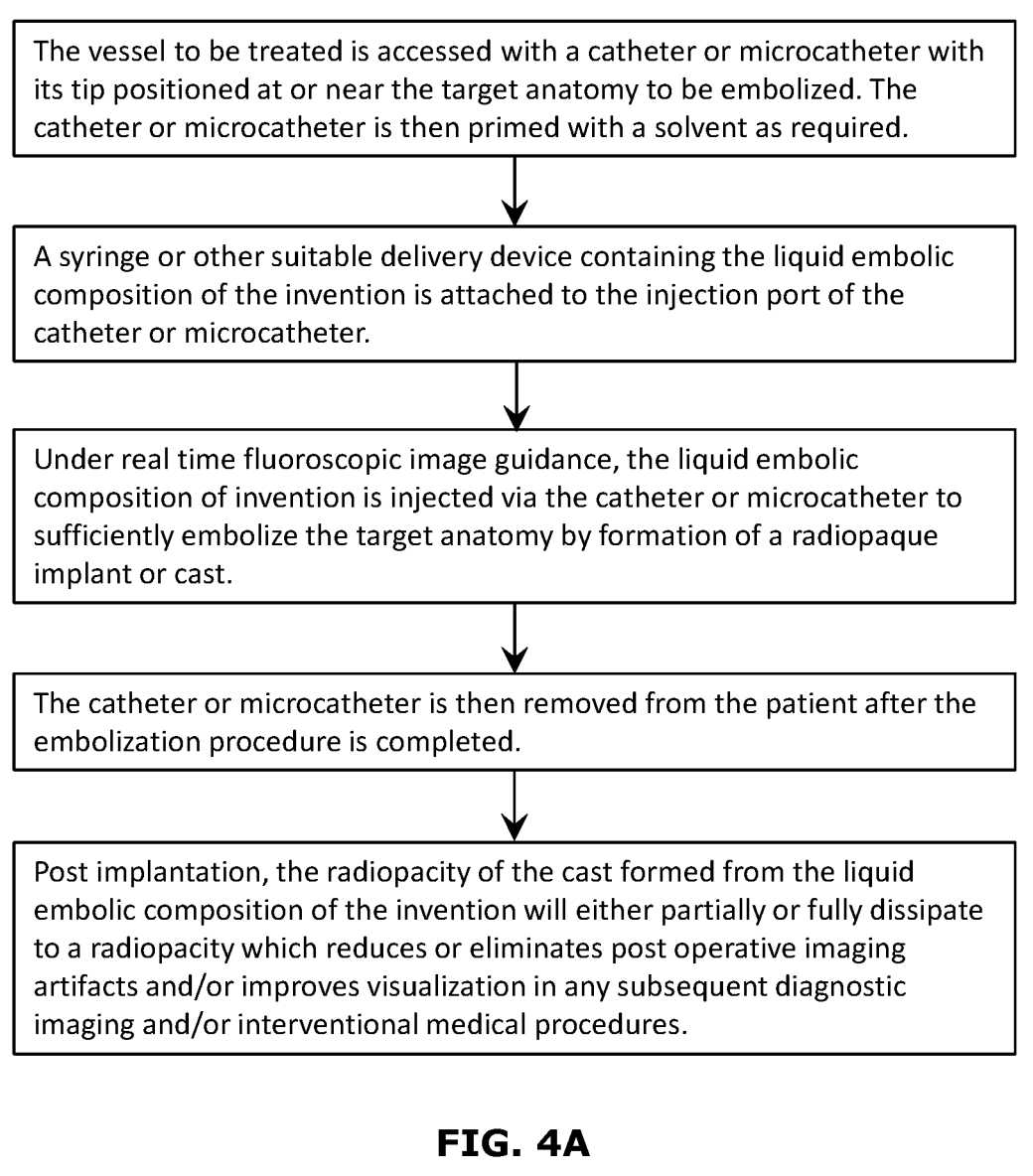

The vessel to be treated is accessed with a catheter or microcatheter with its tip positioned at or near the target anatomy to be embolized. The catheter or microcatheter is then primed with a solvent as required.

↓

A syringe or other suitable delivery device containing the liquid embolic composition of the invention is attached to the injection port of the catheter or microcatheter.

↓

Under real time fluoroscopic image guidance, the liquid embolic composition of invention is injected via the catheter or microcatheter to sufficiently embolize the target anatomy by formation of a radiopaque implant or cast.

↓

The catheter or microcatheter is then removed from the patient after the embolization procedure is completed.

↓

Post implantation, the radiopacity of the cast formed from the liquid embolic composition of the invention will either partially or fully dissipate to a radiopacity which reduces or eliminates post operative imaging artifacts and/or improves visualization in any subsequent diagnostic imaging and/or interventional medical procedures.

FIG. 4A

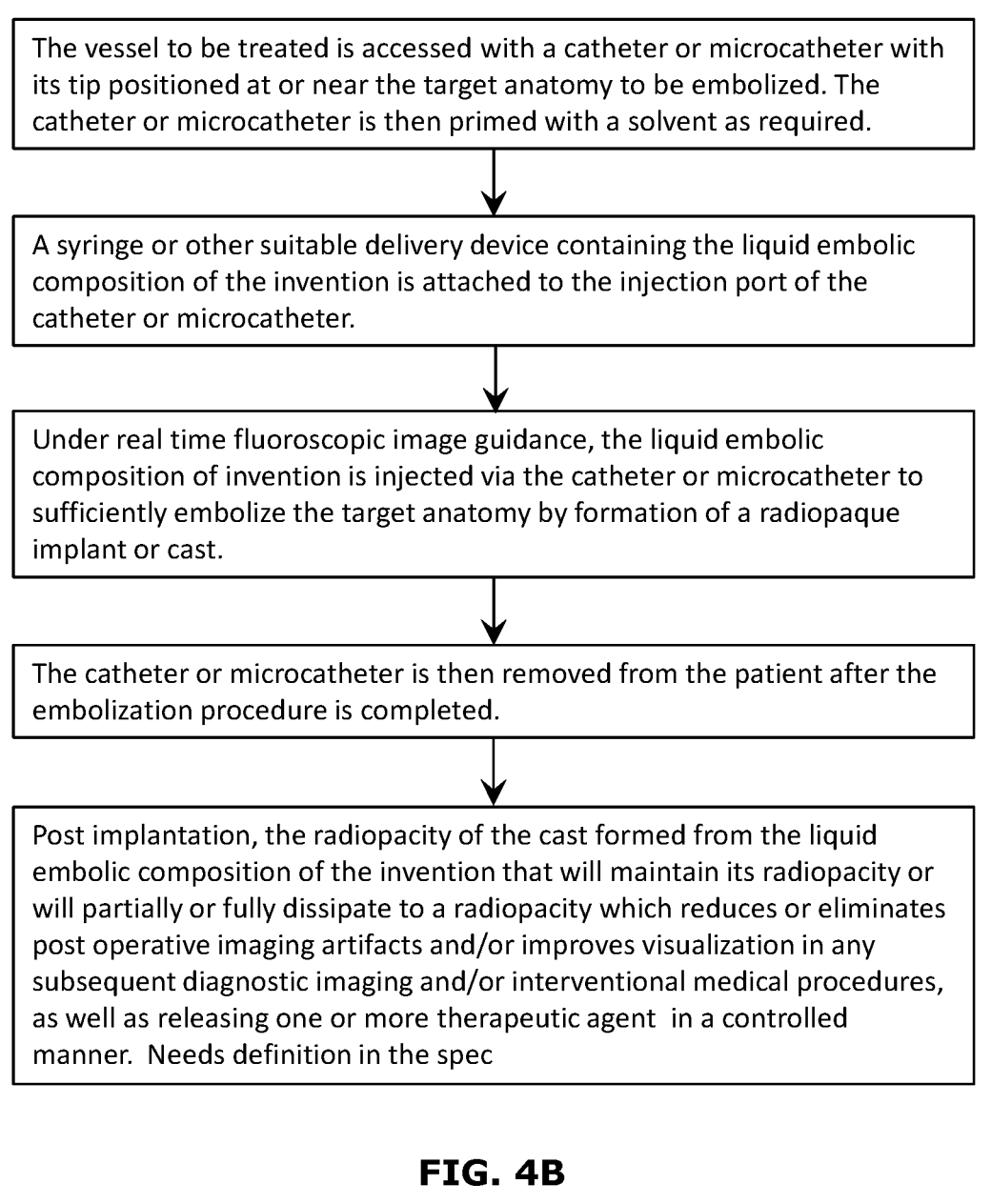

The vessel to be treated is accessed with a catheter or microcatheter with its tip positioned at or near the target anatomy to be embolized. The catheter or microcatheter is then primed with a solvent as required.

↓

A syringe or other suitable delivery device containing the liquid embolic composition of the invention is attached to the injection port of the catheter or microcatheter.

↓

Under real time fluoroscopic image guidance, the liquid embolic composition of invention is injected via the catheter or microcatheter to sufficiently embolize the target anatomy by formation of a radiopaque implant or cast.

↓

The catheter or microcatheter is then removed from the patient after the embolization procedure is completed.

↓

Post implantation, the radiopacity of the cast formed from the liquid embolic composition of the invention that will maintain its radiopacity or will partially or fully dissipate to a radiopacity which reduces or eliminates post operative imaging artifacts and/or improves visualization in any subsequent diagnostic imaging and/or interventional medical procedures, as well as releasing one or more therapeutic agent in a controlled manner. Needs definition in the spec

FIG. 4B

LIQUID EMBOLIC COMPOSITIONS WITH CONTROLLED RELEASE OF RADIOPAQUE AND THERAPEUTIC COMPOUNDS AND METHODS OF USING THE SAME

CROSS-REFERENCE TO RELATED APPLICATIONS

This application claims the benefit of U.S. Provisional Patent Application No. 63/074,924, filed Sep. 4, 2020, which application is incorporated herein by reference in its entirety.

BACKGROUND OF THE INVENTION

Catheter embolization is a common minimally invasive surgical technique that employs technologies or devices to prevent blood flow to an area of the body. These embolic devices are used to treat many debilitating or life threatening medical conditions such as vascular aneurysms, arterio-venous malformations (AVMs), venous or arterial hemor-rhage, endoleaks in the context of endovascular aneurysm repair (EVAR), and hypervascular tumors. For example, embolic devices used for prophylactic treatment of aneu-rysms are implanted into the target vasculature to prevent subsequent rupture and uncontrolled bleeding. In case of hemorrhage, device-based embolization may be used to manage bleeding from an injured vessel which may be inaccessible by other means. Embolization devices may also be used to prepare a tumorous mass for surgical resection by occluding the blood vessels supplying the tumorous mass.

Modern day therapeutic embolization is accomplished with a wide variety of devices including solid, physical forms of devices such as metallic coils, vascular plugs, balloons, covered stents, polymer microspheres, and devices like N-butyl-2-cyanoacrylates (N-BCA) and poly(ethylene-co-vinyl based alcohol) copolymer dissolved in dimethyl sulfoxide (DMSO) that are injected into the body as a liquid and substantially solidify in situ at or near the target anatomy via a phase transition upon contact with blood, water, or other physiological liquids. This variety of devices allows physicians to tailor each procedure on a patient by patient basis depending upon the size and extent of vessels to be blocked and the need to block vessels that are either more proximal or more distal to the tip of the catheter from which they are delivered. Some solid devices such as coils, plugs and balloons lend themselves to more proximal vessel placement due to their inherent physical size limitations (i.e. they simply cannot reach more distal vessels) and as such tend to be used for more discrete or local placement. Other solid devices, such as polymer microspheres which are typically individual micron sized beads, can travel more distally in the vasculature due to the smaller size and are implanted using flow direction after injection into the blood-stream at a location proximal to the intended treatment site. As such, the physicians cannot completely control the loca-tion where the beads will ultimately embolize the target anatomy. On the other hand, liquid embolic devices lend themselves to more controlled delivery and improved distal penetration due to their ability to flow more deeply into a vessel bed as a liquid thereby treating a wider section of the anatomy. Liquid embolic devices can also be more reliable than polymer microspheres since the embolic mass is typi-cally formed and advanced from the delivery catheter tip allowing the physician to maintain control of the embolic agent throughout the procedure. As noted, embolization is often tailored to a given patients need with solid and liquid embolization devices used in combination in order to gain the desired therapeutic effect.

A typical embolization procedure is performed by placing these embolic devices within the target vasculature using standard catheterization technique and equipment such as the use of guide catheters, guide sheaths and/or delivery catheters (e.g. microcatheters) under fluoroscopic guidance. Precise placement and real time monitoring of these embolic devices by fluoroscopic guidance is feasible because these devices are typically radiopaque and this radiopacity allows the physician operator to more safely control the placement of the implant and limit/prevent embolization of non target blood vessels. The radiopacity may be an inherent charac-teristic of the embolic device itself as in the cases of metallic coils or embolic plugs, or radiopacity may be imparted onto the device using a radiopaque element dispersed about or within the device. An example of the latter is the Onyx® Liquid Embolic System (Medtronic plc, Ireland), which utilizes micronized tantalum particles dispersed within a precipitating polymeric solution as the radiopaque element. Upon precipitation of the embolic agent in the target vas-culature, the micronized tantalum particles are retained within the embolic mass which forms in situ such that the location of the embolic mass can be carefully monitored by fluoroscopy in real time by the interventionalist during the embolization procedure. In another example, a precipitating polymeric liquid embolic system called PHIL™ (Terumo Corp., Japan) utilizes radiopaque iodine covalently bonded to the precipitating polymer to provide radiopacity to the liquid embolic suspension and the precipitated embolus. These types of embolic systems generally impart a consis-tent level of radiopacity to the embolic mass and the radiopaque component is permanently incorporated into the embolic structure.

U.S. Pat. Nos. 5,667,767 and 5,695,480 disclose precipi-tating embolic compositions that are rendered radiopaque by including within the composition a dispersed phase of contrast agent wherein the contrast agent is insoluble in water. Likewise, U.S. Pat. Nos. 9,456,823, 10,232,089, and 10,124,090 disclose compositions that are formulated to precipitate in situ, and which are rendered radiopaque by use of a dispersed phase of particulate contrast agent. The particulate contrast agent is disclosed as being soluble or insoluble in water.

While these embolic devices provide important benefits to treat the patients in need, the presence of the radiopaque elements of these devices can introduce undesired effects that persist long after a treatment procedure has been com-pleted. For example, the presence of permanent radiopaque implants in the vascular system may interfere with subse-quent medical imaging procedures (e.g. cone-beam com-puted tomography and magnetic resonance imaging) that may be needed for diagnostic purposes to determine the health condition of the patient. Furthermore, these perma-nent radiopaque implants can impede the planning of sub-sequent stereotactic radiation therapy wherein the dose and dose distribution of radiation may need to be altered to account for the presence of the radiopaque material.

Embolization is sometimes also combined with chemo-therapy in a procedure known as chemoembolization. For example, conventional transarterial chemoembolization (TACE) is performed where the blood vessel supplying a tumor may be occluded after injecting a chemotherapeutic agent into the tumor. This technique traps high levels of chemotherapeutic agent within the tumor by preventing its dissipation in the circulating blood. TACE is most often used to treat inoperable liver cancer or hepatocellular carcinoma, but may also be used in patients whose cancer has metastasized to other areas of the body. TACE may be used as a standalone treatment or in combination with other oncologic procedures including surgery, ablation, standard chemotherapy or radiation therapy. In one example, TACE delivers chemotherapeutic agents directly to the tumor using a catheter positioned within the hepatic artery, which provides the main blood supply to a tumor in the liver. Embolization keeps the chemotherapeutic agent from being washed away from around the tumor site, making it more effective while also reducing the systemic side effects due to the injection being directly into the blood supply of the tumor. Another version of TACE is drug eluting bead based TACE or DEB-TACE wherein non-degradable or degradable drug eluting beads are used as embolic system are used to combine both the vessel embolization and drug delivery. In DEB-TACE, small particles such as the previously mentioned polymer microspheres are loaded with chemotherapeutic agents and are injected into an artery supplying a tumor, hereby interrupting the tumor's blood supply and depriving surrounding tissues of nutrition and oxygen. As noted previously, as with non-drug eluting polymer microspheres, drug eluting beads and microspheres are similarly disadvantaged by their flow directed deployment wherein physician operators only have limited control on the ultimate location of the embolization. This presents obvious and significant safety concerns if the bead or microsphere embolization occurs inadvertently in non-target blood vessels and here the effects of the embolization are further exacerbated by the potential deleterious effects of the chemotherapeutic agent.

US patent application 20180353522 discloses a liquid embolic system comprising an anticancer agent and a silk-elastin like protein polymer, wherein the compositions are liquids prior to administration to a subject, but convert to hydrogels upon administration to the subject. U.S. Pat. No. 9,999,676 discloses biodegradable microbeads having improved adsorptive power to anticancer drugs through the use of microbeads comprising an albumin-anionic polymer conjugate in which albumin is amide-bonded to an anionic polymer and is subsequently cross-linked. U.S. Pat. No. 8,940,334 discloses microspheres based on sulphonate-modified N-Fil hydrogel polyvinyl alcohol (PVA) with bound nemorubicin hydrochloride as anti-cancer drug.

The mechanism of drug incorporation limits the active pharmaceutical ingredients (APIs) that can be used in the case of drug eluting beads and microspheres. Microspheres use either an ion exchange method or a swelling process followed by interaction of the drug with ionized side chains. Therefore, typically, only charged, low molecular weight drugs can be incorporated. As noted before, another limitation of these devices is their finite (physical) size which limits their ability to penetrate down to the capillary level of the vessels feeding a tumor. Use of organic solvents such as DMSO has also limited the use of liquid embolic systems for TACE. The dissipation of the DMSO solvent during the precipitation process at administration potentiates burst release of the entire therapeutic payload of the chosen API, amplifying acute local toxicity and resulting in more transient or limited therapeutic effects. Furthermore, injection of the therapeutic agent into the tumor in tandem with embolization of the feeding arteries limits the number of times local chemotherapy can be performed since the artery is occluded and subsequent access to the tumor is progressively blocked. Delivering an API in one bolus also amplifies the local or systemic toxicity effects as well.

The herein disclosed invention provides compositions and methods of using the same incorporate compounds of interest such as APIs or other therapeutic agents within a liquid embolic system and delivering the said therapeutic agents to, at or within the desired anatomical location in a controlled and sustained manner in addition to achieving embolization.

Based upon the numerous limitations noted above, there is a need in the art for a liquid embolic system that can be delivered and implanted through common delivery systems (e.g. microcatheters) with sufficient radiopacity to facilitate close monitoring of the embolic agent during delivery enabling safe implantation into target vessels, but with this radiopacity being transient. That is, it would be desirable for the implanted embolic mass to partially or fully dissipate its radiopacity over time post implantation to enable improved quality of post operative diagnostic imaging (e.g. cone beam CT and/or MRI) and potentially also enabling safer subsequent interventional procedures by reducing or removing imaging obstructions posed by conventional embolic agents. This quality of "transient opacity" is a subject of the herein disclosed invention. Furthermore, it would be desired to combine the ability to embolize a vessel with an API or other compound or therapeutic of interest in the form of a liquid embolic (versus the tandem TACE or DEB-TACE techniques) employed today. In addition to the ability to provide "transient opacity", the inventions of this disclosure can also incorporate API, or other compounds or therapeutics of interest and release them to the desired target location in a controlled and sustained manner The embodiments of the invention disclosed herein describe how these unique functionalities (i.e. transient opacity and/or controlled drug release) can be imparted to a given liquid embolic agent either individually or in combination with each other depending on the desired clinical outcome.

SUMMARY OF THE INVENTION

Devices and methods of the present invention are liquid embolic devices or systems that comprise embolic materials capable of changing from a substantially liquid state to a substantially solid state upon contact with blood or other aqueous solutions which also incorporate a "compound of interest". This compound of interest may be incorporated for the purposes of providing additional functionality to the liquid embolic device such as temporary radiopacity which enables fluoroscopic visualization during an interventional procedure and/or for imparting therapeutic function that is intended to be released from the liquid embolic in a controlled and sustained manner.

In one example, the liquid embolic system may be composed of a polymer which transitions from liquid to solid upon implantation due to gelation such as a thermo-responsive polymer. In another example, the liquid embolic system may be composed of a polymer dissolved in an organic solvent that precipitates upon contact with blood or aqueous solution. The latter example can be a liquid embolic system comprised of, for example, of an EVOH polymer dissolved in a DMSO solvent.

As noted, the compound of interest may comprise any therapeutic agent that provides treatment to a patient. This agent may include, but is not limited to various APIs or drugs, radioactive materials (e.g. yttrium 90), other radio-pharmaceuticals, and biologics including proteins, peptides, genes, or any other pharmaceutically active ingredient. The compound of interest may further be composed of a combination of therapeutic agents and radiopaque agents imparting multiple desirable functionalities to the liquid embolic.

The embodiments of this invention envision that the time-frames over which said therapeutics and/or radiopaque agents elute or dissipate could be variable or the same and/or generally customized as desired for targeted clinical outcomes or procedures. For example, it may be desirable for the radiopacity to dissipate or fade over a one month period post operatively while it may also be desirable to release an API over a more sustained period (e.g. 3-6 months or more) in a controlled manner Alternatively, there may be instances where it is desirable to maintain the radiopacity of the embolic agent while only the API dissipates post operatively.

The compound of interest may be incorporated within the liquid embolic system in various forms and using a variety of techniques. In one example, the compound of interest is physically mixed with the liquid embolic agent using commonly available techniques such as mixing, grinding, spinning, spray drying, etc. In this example, the compound of interest is either fully or partially soluble in aqueous media by nature or has been made soluble or partially soluble using variety of techniques such as micronization, PEGylation, etc. and the release of the compound of interest from the liquid embolic system is inherently controlled by its rate of solubility and the rate by which it can diffuse out of the substantially solidified embolus.

In another example the compound of interest is chemically bound to the embolic polymer. In this scenario, the chemical linkages between the compound of interest and the embolic polymer may be broken via a variety of mechanisms such as hydrolysis or enzymatic degradation. This results in release of the compound of interest with the ratio of release of the compound of interest from the embolic mass controlled by the rate at which such linkages are broken and the rate of the diffusion of the compound of interest out the substantially solidified embolic mass.

In another example, the compound of interest is physically encapsulated within a carrier. The encapsulation of the compound of interest in a carrier can occur prior to mixing with the liquid embolic system or can occur within the liquid embolic e.g. using emulsification techniques. The carrier can be in various physical forms. For example, the carrier can be in the form of microspheres or nanospheres, micelles, dendrimers, liposomes or lipid nanoparticles. In this scenario, the rate of release of the compound of interest from the embolic mass is controlled by the dissolution or degradation rate of the carrier and the rate of the diffusion of the compound of interest out of the substantially solidified embolic mass.

In another example, it is herein envisioned that rather than physical encapsulation in a carrier, the compound of interest may be physically or chemically bound to a carrier. An example of physical binding is applying the compound of interest on the surface of the carrier (e.g. in a core-shell structure). An example for chemical binding is modifying the surface of the carrier so that it can form a chemical linkage with the compound of interest. The carrier can come in various physical forms including microspheres, nano spheres, micelles, dendrimers, liposomes or lipid nanoparticles. In this scenario, the ratio of release of the compound of interest from the embolic mass is controlled by the rate by which the chemical linkages to the carrier are broken and/or the rate of dissolution or degradation of the carrier releasing the compound of interest.

The inventions described herein also envision several mechanisms that can be employed to control the rate of release of the compound of interest from the embolic mass such as adjusting the permeability of the embolic mass to either hinder or promote diffusion of the compound of interest out of the embolic mass an into the surrounding environment. In one embodiment, various additives (e.g. pore forming agents) can be added to the liquid embolic formulation to adjust the permeability of the embolic mass. For example, diffusion of the compound of interest may be enabled and facilitated by presence of water-soluble pore formers dissolved or suspended within the liquid embolic system, wherein the pore formers create channels and pathways for the compound of interest to elute or dissipate from the substantially solid embolic mass after implantation.

Other mechanisms that can be used to further improve the performance of the liquid embolic of this composition include emulsifying or suspending agents that can facilitate the dispersion of the compound of interest within the liquid embolic material. In another example, thickeners can be used to adjust the viscosity of the liquid embolic, facilitating its safe and controlled delivery. In yet another example, additives may be added to the liquid embolic to impart thixotropic properties to the liquid.

As described previously, the devices and methods of this invention are intended to provide various functionalities optimized for its clinical use such as transient radiopacity. In this scenario, the compound of interest is a radiopaque agent. Using the embodiments described herein, it is envisioned that during an embolization procedure, the liquid embolic composition is injected into the target vasculature where the substantially liquid embolic undergoes a phase change to a substantially solid state entrapping the radiopaque agent, impeding the flow of blood with the radiopaque agent remaining dispersed within the embolic mass as is done currently. However, after the completion of the embolization procedure, the radiopaque agent slowly and predictably dissipates, elutes, or diffuses out of the substantially solid embolic mass where it can be excreted from the body of the patient. As a result of the outbound diffusion or dissipation of the radiopaque agent, the embolic mass can lose some or all of its radiopacity over time. The rate of release of the radiopaque agent can have kinetics that include burst release of the radiopaque agent, zero-order release, first-order release, delayed burst release, delayed zero-order release, delayed first-order release, or combinations thereof.

Similarly and in another example, the compound of interest included in the liquid embolic composition may be a therapeutic agent, and the composition can be used to perform a TACE procedure or the like. In one such scenario, the composition is injected into the target vasculature feeding a tumor where the liquid embolic undergoes a phase change to a substantially solid state entrapping the therapeutic agent while also impeding the flow of blood or effectively embolizing the vessel. Initially, all or most of the chosen therapeutic agent remains dispersed within the embolic mass, but subsequently slowly and predictably diffuses out of the embolic mass and into tumor post implantation to exert its therapeutic benefit. The presence of the embolic mass ensures that the therapeutic agent can not be easily washed out from the site of action thereby maintaining its concentration above the therapeutic level. As noted for the radiopaque compound of interest, the rate of release of a therapeutic agent as a compound of interest can also have kinetics that include burst release, zero-order release, first-order release, delayed burst release, delayed zero-order release, delayed first-order release, or combinations thereof.

It should be clear to one of skill in the art that these examples are not exclusive; any number of these mechanisms may be combined in a single embolic composition to achieve a desired functionality. For example, one could envision a liquid embolic composition of the invention used for a TACE procedure where the compound of interest is a combination of a radiopaque agent and a therapeutic agent, where each of these agents are released at the same or different rate or kinetic of release. In this example the release of the radiopaque agent imparts transient radiopacity to the embolic mass and the controlled release of the therapeutic agent results in the shrinkage of a tumor over time.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 3G depicts a graphical representation of the release kinetics of the compound of interest in the embolic composition provided in FIG. 3F.

FIG. 3H depicts a longitudinal cross sectional view of a blood vessel embolized using a liquid embolic composition of the invention containing one compound of interest dispersed within it and another compound of interest encapsulated in a carrier also dispersed within it.

FIG. 3I depicts a longitudinal cross sectional view of a blood vessel embolized using the liquid embolic composition provided in FIG. 3H after complete release of one of its compounds of interest.

FIG. 4A provides a typical method of using a liquid embolic composition of invention which provides transient radiopacity.

FIG. 4B provides a typical method of using a liquid embolic composition of invention which provides transient radiopacity and controlled release of therapeutic agent.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a compound" includes a plurality of such compounds and reference to "the polymer" includes reference to one or more polymer and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1A:
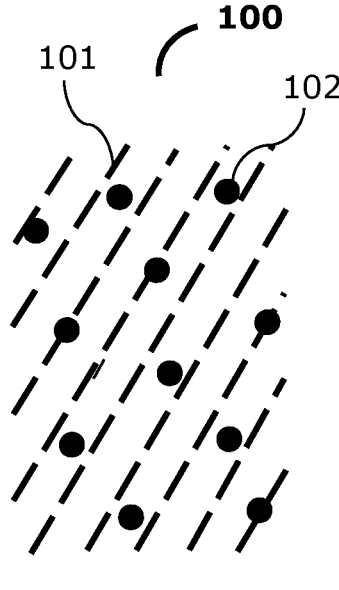
FIG. 1A provides a graphical representation of a liquid embolic composition of the invention with a compound of interest dispersed within it.
Figure 1B:
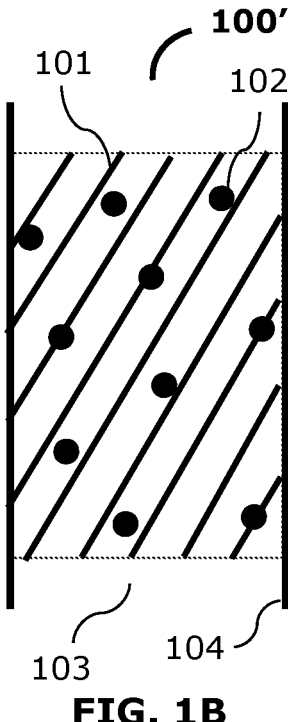
FIGS. 1B through 1D depict longitudinal cross sectional views of a blood vessel embolized using an embolic composition of the invention containing a compound of interest dispersed within it that dissolves and diffuses out of the composition over time.
Figure 1C:
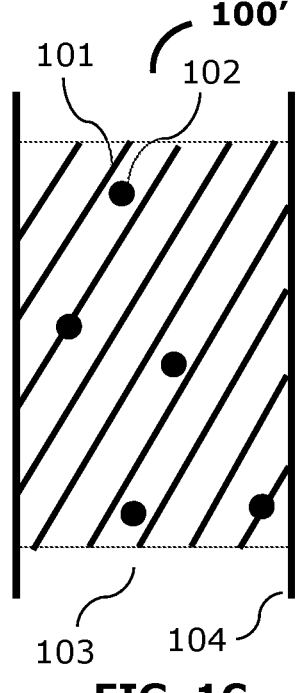
Figure 1D:
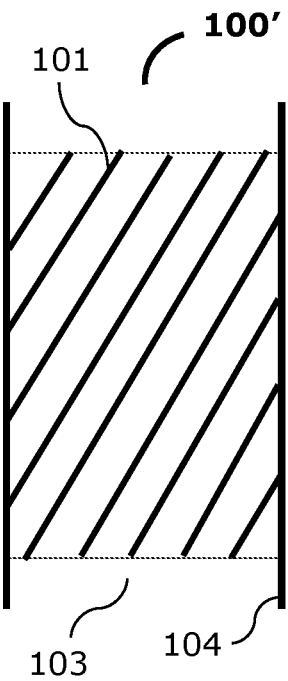

FIGS. 1A through 1D are graphical representations of one embodiment of a liquid embolic composition of the invention containing a compound of interest 102, depicting the phase change or transformation from a substantially liquid embolic composition 100 to a substantially solid embolic composition 100', as well as the reduction in concentration of the compound of interest 102 in the substantially solid composition 100' due to solubility and diffusion. FIG. 1A depicts the embolic composition 100 of this invention in a substantially liquid state and ready for injection into vessel lumen 103. In FIG. 1A, substantially liquid embolic composition 100 is illustrated by dashed lines and comprises embolic material 101 with compound of interest 102 incorporated within it. FIG. 1B depicts a longitudinal cross section view of a blood vessel with lumen 103 and vessel walls 104. In FIG. 1B, the substantially liquid embolic composition 100 previously shown in FIG. 1A is transformed to a substantially solid embolic composition 100' (represented by solid lines) after injection into blood vessel lumen 103, thereby embolizing or occluding the blood vessel. In addition, the substantially solid embolic composition 100' shown in FIG. 1B surrounds and entraps compound of interest 102 within the embolized or occluded vessel segment. FIG. 1C depicts the entrapped compound of interest 102 at a reduced concentration compared to that depicted in FIG. 1B. The reduction in concentration as illustrated in the transition from FIG. 1B to FIG. 1C may be driven by the dissolution and/or diffusion of compound of interest 102 in the presence of media (not shown) permeating the substantially solid embolic composition 100'. The media (not shown) may be a physiological media such as blood, plasma, water, and the like. Further progression of time may eventually lead to full dissolution and/or diffusion of compound of interest 102 out of substantially solid embolic composition 100' as depicted in FIG. 1D leaving behind only embolized or occluded vessel lumen 103. It should be obvious to those of skill in the art that the figures provided herein are not drawn to scale and are magnified for illustrative purposes and clarity only. For example, it is envisioned that compound of interest 102 shown in FIGS. 1A to 1C would likely be substantially smaller (i.e. micron sized or potentially nano-sized).

In one embodiment, the compound of interest 102 shown in FIG. 1B is a radiopaque agent. As a result of the presence of the radiopaque agent (i.e. compound of interest 102), the substantially solid embolic composition 100' shown in FIG. 1B may be highly radiopaque, while the substantially solid embolic composition 100' shown in FIG. 1C may be less radiopaque, but still visible under fluoroscopic examination. The reduced radiopacity may correspond to dissolution and/or diffusion of the radiopaque agent out of embolic composition 100'. FIG. 1D depicts the substantially solid embolic composition 100' after the radiopaque agent has completely dissolved and/or diffused out of the embolic composition 100'. It should be clear to one of skill in the art that a clinically significant reduction in radiopacity does not necessarily require all, or even a majority, of the radiopaque agent to diffuse out of substantially solid embolic composition 100'. The threshold of a clinically useful reduction in radiopacity may be determined by the clinical requirements of a particular medical procedure, and the amount of diffusion of the radiopaque agent required to reach that threshold may be variable and dependent on the characteristics of the radiopaque agent used in a given composition. For example, a highly radiopaque agent may require that over 90% of the radiopaque agent diffuse out of the embolic mass or substantially solid embolic composition 100' to obtain a clinically significant reduction in radiopacity, while a less radiopaque agent may only require 50% of the radiopaque agent to diffuse out of the embolic mass or substantially solid embolic composition 100' to obtain a clinically significant reduction in radiopacity. Likewise, the threshold for clinically significant initial radiopacity (i.e. having enough radiopacity to achieve the desired clinical or procedural outcomes at the time of the procedure) may vary depending on the medical procedure and site of embolization. For example, a substantially liquid embolic composition 100 used to treat neurovasculature may need to be more radiopaque to achieve a reasonable signal when imaging through the skull, while a substantially liquid embolic composition 100 used to treat a peripheral vascular arteriovenous malformations may require substantially less radiopacity at the time of use.

In another embodiment, the compound of interest 102 shown in FIG. 1B is a therapeutic agent. FIG. 1D depicts substantially solid embolic composition 100' after all of the therapeutic agent has diffused out of substantially solid composition 100'. It should be clear to one of skill in the art that different therapeutic agents have differing therapeutic potency and therefore in order to reach a clinically significant therapeutic outcome the required amount of the therapeutic agent depends on the potency and physiochemical characteristics of the chosen therapeutic agent.

An exemplary composition of a substantially liquid embolic composition 100 of the invention may comprise an embolic material ethylene vinyl alcohol (EVOH) dissolved in dimethyl sulfoxide (DMSO) and mixed with micronized tantalum as a radiopaque agent well known in the art. EVOH is a random copolymer of ethylene and vinyl alcohol monomers that is soluble in DMSO and insoluble in aqueous solutions; varying the ratio of ethylene to vinyl alcohol will change the physical and chemical properties of the EVOH polymer. When introduced into an aqueous solution, the DMSO will rapidly diffuse into the aqueous media, causing the EVOH to precipitate into a cohesive embolic mass about the radiopaque tantalum particles. This mass has a permeability with respect to the radiopaque agent that is a based on several parameters, including, but not limited to the mole % of ethylene in the EVOH copolymer, the size of the radiopaque tantalum particles, the viscosity of the EVOH/DMSO liquid embolic solution, and the like.

In general, a larger amount of ethylene content in the EVOH copolymer will result in a tougher embolic mass after precipitation while a smaller amount of ethylene content in the EVOH copolymer will result in a looser, more gel-like embolic mass after precipitation. Preferred mole percentages of ethylene may include 25 to 29 mole %, 29 to 34 mole %, 34 to 42 mole %, 42 to 46 mole %, 46 to 50 mole %, and over 50 mole %. The ratio of EVOH to DMSO may be varied to produce a solution with a range of viscosities; it is preferable to have solutions with the following viscosities (as measured at 40° C.): less than 7 centistokes (cSt), 7 to 9 cSt, 9 to 11 cSt, 11 to 13 cSt, 13 to 15 cSt, 15 to 17 cSt, 17 to 19 cSt, 19 to 21 cSt, 21 to 23 cSt, 23 to 25 cSt, 25 to 27 cSt, 27 to 29 cSt, 29 to 31 cSt, 31 to 33 cSt, 33 to 35 cSt, or greater than 35 cSt. The exemplary composition may further comprise a dispersed compound or multiple compounds of interest 102, preferably having a finite and low saturated solubility in water. By saturated solubility, it is meant that a solid compound of interest 102 may be added to an aqueous solution of that compound of interest 102 held at 37° C. and the addition of more solid compound of interest 102 causes no net increase in the concentration of the compound of interest 102 dissolved in the liquid phase of the solution.

In one embodiment where the compound of interest 102 in substantially solid embolic composition 100' is a radiopaque agent, the selected radiopaque agent may be chosen from, but is not limited to the following compounds: barium, barium salts, bismuth, bismuth subsalicylate, bismuth subgallate copper, silver, potassium iodide, iodine, calcium iodate, platinum, tantalum, titanium, tungsten, and zirconium. Preferred radiopaque agents may include iodate salts such as silver iodate, calcium iodate, zinc iodate dehydrate, ammonium iodate, magnesium iodate, potassium iodate, and sodium iodate. A radiopaque agent with finite and low solubility includes compounds that have saturated aqueous solubilities in the range of 0.01 mg/ml to about 20 mg/ml. A more preferred solubility value is in the range of 0.01 mg to about 10 mg/ml. The most preferred compounds are those with saturated solubility values in the range of 0.01 mg to about 5 mg/ml.

In the previously mentioned EVOH/DMSO/tantalum liquid embolic composition 100, if the radiopaque tantalum particles were replaced with a compound of interest 102 comprised of a radiopaque agent that can effectively diffuse or be dissolved from the embolic mass or substantially solid embolic composition 100', the rate of dissolution and/or diffusion may be controlled by the permeability of the substantially solid embolic composition 100' with respect to the radiopaque agent and the saturated aqueous solubility of the radiopaque agent. If the permeability of the substantially solid embolic composition 100' with respect to the radiopaque agent is high, and the saturated aqueous solubility of the radiopaque agent is also high, the radiopaque agent will rapidly dissolve into the aqueous media and rapidly diffuse out of the substantially solid embolic composition 100', quickly decreasing the radiopacity. On the other hand, if the permeability of the substantially solid embolic composition 100' with respect to the radiopaque agent is low, but the saturated aqueous solubility of the radiopaque agent is high, the radiopaque agent will rapidly dissolve into the aqueous media and slowly diffuse out of the substantially solid embolic composition 100', decreasing the radiopacity at a moderate rate. Alternatively, if the permeability of the substantially solid embolic composition 100' with respect to the radiopaque agent is high, but the saturated aqueous solubility of the radiopaque agent is low, the radiopaque agent will slowly dissolve into the aqueous media then rapidly diffuse out of the substantially solid embolic composition 100', decreasing the radiopacity at a moderate rate. In yet another alternative, if the permeability of substantially solid embolic composition 100' with respect to the radiopaque agent is low, and the saturated aqueous solubility of the radiopaque agent is also low, the radiopaque agent will slowly dissolve into the aqueous media then slowly diffuse out of the substantially solid embolic composition 100', decreasing the radiopacity at a low rate. It should be clear to one of skill in the art that the terms "rapid", "moderate", and "low" are relative, and that the parameters driving the rate of change of the radiopacity of substantially solid embolic composition 100' may be adjusted or modified to obtain a desired or targeted or specified rate of change in radiopacity of the substantially solid embolic composition 100' that is suitable for a specific clinical application of the substantially liquid embolic composition 100. It should also be clear to one of skill in the art that the rate of precipitation of the substantially liquid embolic composition 100, the rate of diffusion of the organic solvent into the aqueous media, and the rates of dissolution and diffusion of the radiopaque agent are not necessarily on the same time scale either. For example, the precipitation of substantially liquid embolic composition 100 may occur on a time scale of seconds, while the complete diffusion of DMSO out of the substantially solid embolic composition 100' may occur on a time scale of tens of minutes, and the dissolution and diffusion of the radiopaque agent out of substantially solid embolic composition 100' may occur on a time scale of days, weeks, months, or years or alternatively be designed to stay constant permanently.

An exemplary composition of a substantially liquid embolic composition 100 of the invention may comprise a solution of ethylene vinyl alcohol (EVOH) dissolved in dimethyl sulfoxide (DMSO). This exemplary composition may further comprise a dispersed compound of interest 102 comprising a therapeutic agent or agents, preferably having a finite and low saturated solubility in water. The said therapeutic agent or agents may include, but are not limited to anti-neoplastic drugs such as alkylating agents, antimetabolites, antibiotics, plant alkaloids and hormonal agents, anti-angiogenic compounds, and radioactive materials (e.g. yttrium 90), or other radiopharmaceuticals like radioactive iodine. Preferred therapeutic agents may include plant alkaloids such as paclitaxel or irinotecan, or anthrocycline antibiotics such as doxorubicin, tetracycline, idarubicin and mitomycin. A therapeutic agent with finite and low solubility includes compounds that have the part of the solvent required per part of solute in the range of 30 to about 10000. A more preferred solubility value is in the range of 100 to about 10000. The most preferred compounds are those with solubility values in the range of 100 to about 1000. As previously noted, when introduced into aqueous media, the EVOH will precipitate around the therapeutic agent to form a substantially solid embolic composition 100'. Substantially solid embolic composition 100' will have a permeability with respect to the radiopaque agent that is a based on several parameters, including but not limited to the mole % of ethylene in the EVOH copolymer, the size of the therapeutic agent, the viscosity of the EVOH/DMSO solution, and the like.

Figure 2A:
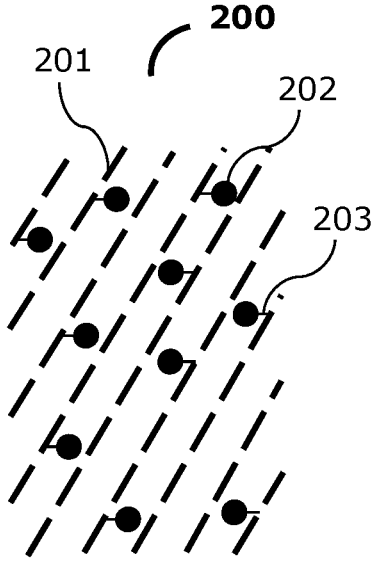
FIG. 2A provides a graphical representation of a liquid embolic composition of the invention with a compound of interest chemically bonded to the embolic material.
Figure 2B:
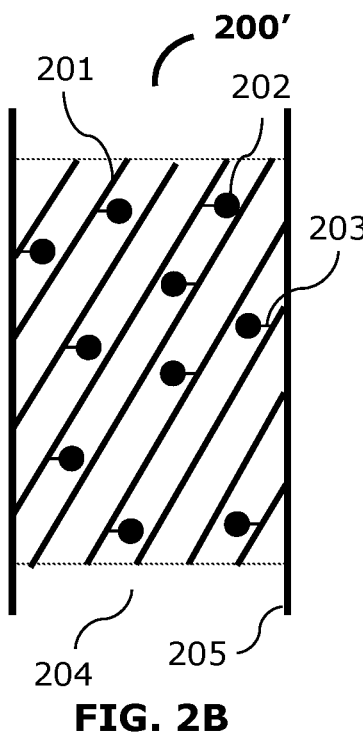
FIGS. 2B through 2D depict longitudinal cross sectional views of a blood vessel embolized using the liquid embolic composition of FIG. 2A illustrating the release and diffusion of the compound of interest via cleavage of the chemical bonds over time.

FIGS. 2A through 2D are graphical representations of another embodiment of a liquid embolic composition of the invention. FIG. 2A depicts the substantially liquid embolic composition 200 comprising embolic material 201, as represented by dashed lines bound to compound of interest 202 through chemical bond 203. FIG. 2B depicts a longitudinal cross sectional view of a blood vessel with lumen 204 and vessel walls 205. In FIG. 2B, the substantially liquid embolic composition 200 previously shown in FIG. 2A is transformed to a substantially solid embolic composition 200' (represented by solid lines) after injection into blood vessel lumen 204, thereby embolizing or occluding the blood vessel. In FIG. 2B, the compound of interest 202 remains unchanged through the solidification of embolic composition from a substantially liquid state 200 to a substantially solid state 200'.

Figure 2C:
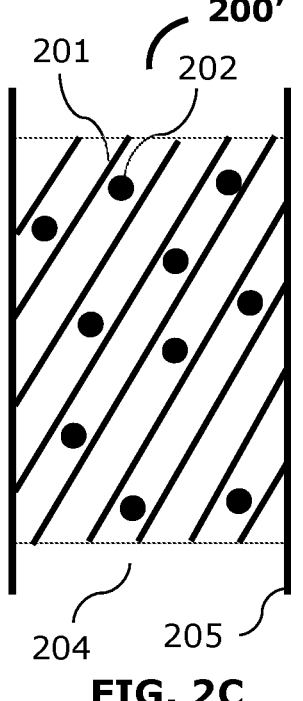
Figure 2D:
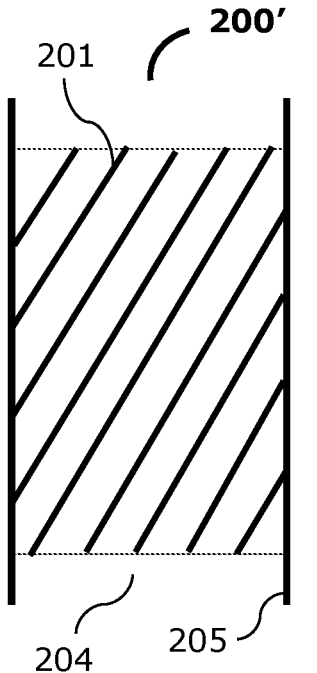

FIG. 2C depicts the same substantially solid embolic composition 200' of FIG. 2B after chemical bond 203 binding the compound of interest 202 to substantially solid embolic composition 200' has been broken or cleaved (e.g. by hydrolysis or enzymatic degradation and the like). As a result, compound of interest 202 is free to dissolve and/or diffuse out of substantially solid embolic composition 200' and enter the blood flow or adjacent tissues (not shown) to provide a therapeutic effect and to subsequently be excreted from the body. FIG. 2D depicts the substantially solid embolic composition 200' completely depleted of compound of interest 202 wherein embolic material 201 continues to maintain occlusion of the embolized blood vessel segment. Chemical bond 203 can be in a variety of forms including, but not limited to electrostatic bonding, covalent bonding, dipole-dipole attraction, ionic bonding, metallic bonding or hydrogen bonding. As noted previously, the breaking or cleavage of chemical bond 203 may occur through a variety of mechanisms such as hydrolysis, photodegradation, or through biological processes such as lysis or enzymatic degradation or combinations thereof and may be driven primarily by permeation of blood or other biological fluids (not shown) into the substantially solid embolic composition 200'. It should be obvious to those of skill in the art that the figures provided herein are not drawn to scale and are magnified for illustrative purposes and clarity only. For example, it is envisioned that compound of interest 202 and bond 203 shown in FIGS. 2A to 2C would likely be substantially smaller (i.e. micron sized, nano-sized or even smaller).

In one embodiment, the compound of interest 202 shown in FIG. 2A is a radiopaque agent chemically bound to the embolic material 201 via chemical bond 203. As a result of the presence of the chemically bound radiopaque agent (i.e. compound of interest 202), the substantially solid embolic composition 200' shown in FIG. 2B may be highly radiopaque after delivery and implantation in a blood vessel lumen 204. With the passage of time, the substantially solid embolic composition 200' shown in FIG. 2B to that shown in FIG. 2C wherein chemical bonds 203 have been broken or cleaved. As shown in FIG. 2C, the unbound compound of interest 202 (i.e. radiopaque agent in this example) is shown entrapped within substantially solid embolic composition 200' in a manner similar to what was described previously in FIG. 1B. In practice, the number of chemical bonds 203 broken or cleaved (i.e. by hydrolysis, enzymatic degradation or the like) may not necessarily happen all at once and instead may break or cleave over time. Either way, it would be expected that as chemical bonds 203 are broken or cleaved, the radiopaque agent is free to dissolve and/or diffuse out of substantially solid embolic composition 200', resulting in a reduction in radiopacity or more broadly transient radiopacity. Finally, FIG. 2D depicts substantially solid embolic composition 200' implanted within vessel lumen 204 after the radiopaque agent has completely dissolved and/or diffused out of substantially solid embolic composition 200' leaving behind only a substantially or completely radiolucent embolic material 201. It should be clear to one of skill in the art that a clinically significant reduction in radiopacity does not necessarily require all, or even a majority, of the radiopaque agent to diffuse out of substantially solid embolic composition 200' to render the implant non obstructive to future diagnostic imaging or therapeutic procedures.

In another embodiment, the compound of interest 202 shown in FIG. 2A is a therapeutic agent, such as an active pharmaceutical ingredient (API). As chemical bond 203 breaks down therapeutic agent (i.e. compound of interest 202) is released from substantially solid embolic composition 200' and can diffuse to its intended target site (e.g. inside a cancerous tumor—not shown). The rate of release of therapeutic agent 202 depends on the rate and ease by which biological fluids can permeate through substantially solidified embolic composition 200' and the rate of breakdown of chemical bond 203. For example, a highly permeable, substantially solid embolic composition 200' can result in a higher rate of release of therapeutic agent 202 compared to a less permeable, substantially solid embolic composition 200'. In this embodiment, the therapeutic agent or agents preferably have a finite and low saturated solubility in water. The said therapeutic agent or agents may include, but are not limited to anti-neoplastic drugs such as alkylating agents, antimetabolites, antibiotics, plant alkaloids and hormonal agents, anti-angiogenic compounds, and radioactive materials (e.g. yttrium 90), or other radiopharmaceuticals like radioactive iodine. Preferred therapeutic agents may include plant alkaloids such as paclitaxel or irinotecan, or anthrocycline antibiotics such as doxorubicin, tetracycline, idarubicin and mitomycin. A therapeutic agent with finite and low solubility includes compounds that have the part of the solvent required per part of solute in the range of 30 to about 10000. A more preferred solubility value is in the range of 100 to about 10000. The most preferred compounds are those with solubility values in the range of 100 to about 1000.

In yet another embodiment of the invention shown in FIGS. 2A to 2D, compound of interest 202 may be composed of a combination of one or more radiopaque agents and one or more therapeutic agents, each connecting to the embolic material 201 through similar or differing chemical bonds 203. In a scenario where a combination of radiopaque agent(s) and/or therapeutic agent(s) are used, the rate of release of each of the agents could be similar or different in relation to each other. The radiopaque and therapeutic agents can be encapsulated or dispersed within the substantially solid embolic composition 200' using differing methods. For example, a radiopaque agent could be physically entrapped within the substantially solid embolic composition 200' as shown in FIG. 1B and a therapeutic agent bound to the embolic material 201 via chemical bonds 203 as shown in FIG. 2B.

Figure 3A:
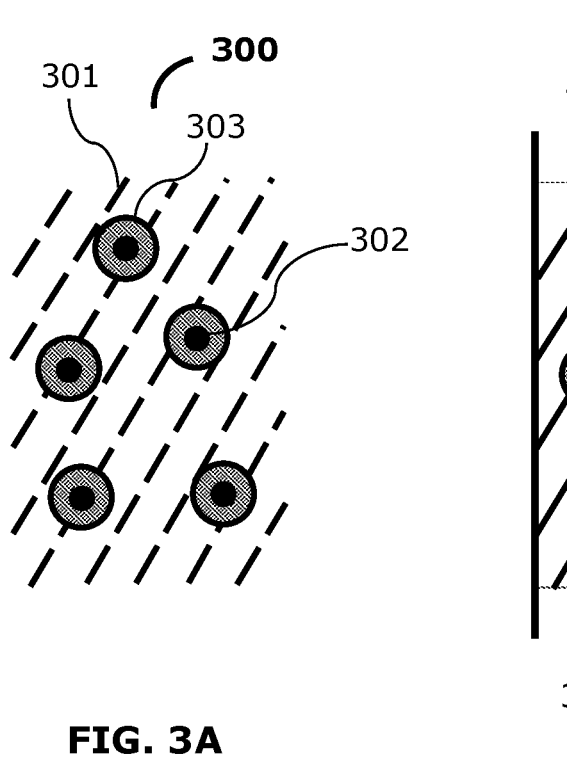
FIG. 3A provides a graphical representation of a liquid embolic composition of the invention with a compound of interest encapsulated in a carrier dispersed within it.
Figure 3B:
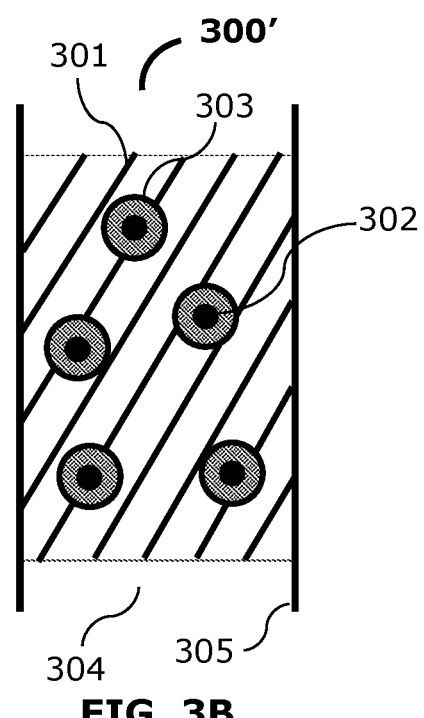
FIGS. 3B through 3D depict longitudinal cross sectional views of a blood vessel embolized using the liquid embolic composition of FIG. 3A illustrating the release and diffusion of the compound of interest after dissolution and degradation of the carrier over time.
Figure 3C:
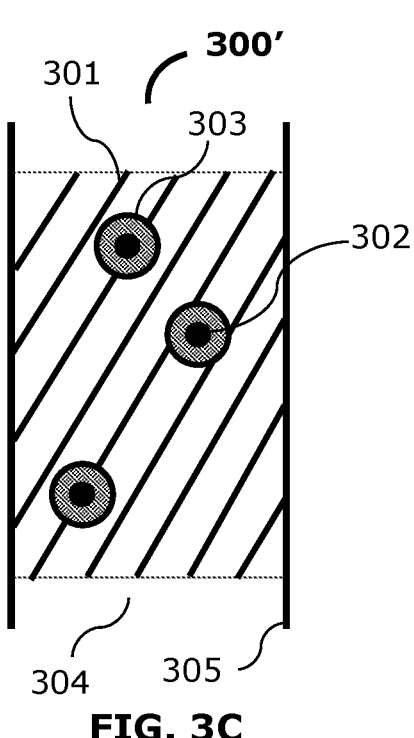
Figure 3D:
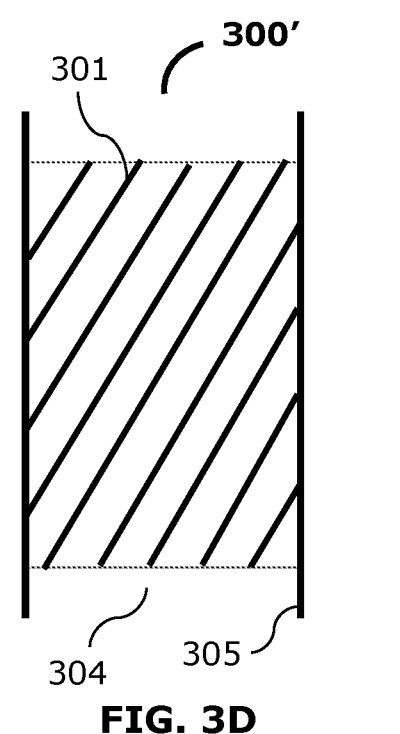

FIGS. 3A through 3D are graphical representations of one embodiment of a substantially liquid embolic composition of the invention. FIG. 3A depicts the embolic composition 300 of this invention in a substantially liquid form and ready for injection into vessel lumen 304. In FIG. 3A, substantially liquid embolic composition 300 is illustrated by dashed lines and comprises embolic material 301 with compound of interest 302 encapsulated within a biocompatible carrier 303. Carrier 303 is substantially insoluble within substantially liquid embolic composition 300. FIG. 3B to 3D depict a longitudinal cross sectional view of a blood vessel with lumen 304 and vessel walls 305. In this figure, the substantially liquid embolic composition 300 previously shown in FIG. 3A is transformed to a substantially solid embolic composition 300' (represented by solid lines) after injection into blood vessel lumen 304, thereby embolizing or occluding the blood vessel. In addition, the substantially solid embolic composition 300' shown in FIG. 3B surrounds and entraps the carriers 303 encapsulating the compound of interest 302 within the embolized or occluded vessel segment. FIG. 3C depicts a reduction in the number of carriers 103 within the substantially solid embolic composition 300' as a result of dissolution, degradation or diffusion of carrier 303 in the presence of media (not shown) and/or enzymes permeating the substantially solid embolic composition 300'. The media (not shown) may be a physiological media such as blood, plasma, water and the like. In one scenario carrier 303 is substantially broken down, and compound of interest 302 is then free to dissolve and/or diffuse out of substantially solid embolic composition 300'. It is also possible for carrier 303 to simply diffuse out the substantially solid embolic composition 300'. In this scenario, the carrier 303 can release the compound of interest 302 at the intended target site, such as within a cancerous tumor (not shown). Further progression of time may eventually lead to full dissolution, degradation and/or diffusion of all or most remaining carriers 303, as well as all or most of the compound of interest 302 released from substantially solid embolic composition 300' as depicted in FIG. 3D leaving behind only embolic material 301 in vessel lumen 304. It should be obvious to those of skill in the art that the figures provided herein are not drawn to scale and are magnified for illustrative purposes and clarity only. For example, it is envisioned that carrier 303 and/or the compound of interest 302 shown in FIGS. 3A to 3C would likely be substantially smaller (i.e. micron sized or potentially nano-sized).

The rate of reduction of carriers 303 incorporated in the substantially solid embolic composition 300' in FIG. 3B to that shown in FIG. 3C depends on the size, chemical composition, rate of solubility, and susceptibility of carrier 303 to breakdown through hydrolysis or other biological processes (e.g. enzymatic degradation). Examples of materials that can be used to form carrier 303 include, but are not limited to polymers consisting of any saturated or unsaturated hydrocarbons, ester, amide or ether bonds, argo-polymers such as polysaccharides, proteins such as albumin, natural polymers such as alginates and cellulose, synthetic polyesters and co-polymers thereof, polyurethanes, bioceramics, bioglasses, dendrimers such as poly(amidoamine), lipids such as triglycerides, and polar oils, phospholipids such as hydrogenated phosphatidylcholine, polar or non-ionic surfactants, and combinations thereof.

It would be apparent to one skilled in the art that the volume fraction of carrier 303 in substantially solid embolic composition 300' can impact the rate of release of compound of interest 302. For example, at higher volume fractions of carrier 303, an interconnected porous structure can be created upon dissolution, degradation and/or diffusion of carriers 303 allowing for easier liquid access to the interior of substantially solid embolic composition 300' resulting in higher rate of release of compound of interest 302. Preferred volume fraction of carrier 303 within substantially solid embolic composition 300' may be from 1 to 80 v/v % or preferably 5 to 50 v/v % and even more preferably from 5 to 30 v/v %.

Carrier 303 could be in the form of, but not limited to an emulsion, micelle, dendrimer, microsphere, nanosphere, lipid nanoparticle, and liposomes or a combination thereof commonly known in the art. The size of carrier 303 can impact the physical properties of the embolic composition 300 and 300'. For example, larger sizes of carrier 303 could result in deteriorated injectability of substantially liquid embolic composition 300 or negatively impact the ability of substantially liquid embolic composition 300 containing carrier 303 to penetrate down to the capillary level of the vessels. The preferred size of carrier 303 can be in the range of 0.1 to 100 μm or 0.1 to 30 μm or in a more preferred scenario they can fall within 0.1 to 5 μm size range.

There are various methods known to those skilled in the art to create substantially liquid embolic composition 300. For example, compound of interest 302 can be first encapsulated within carrier before mixing with a substantially liquid embolic composition 300. Alternatively, carrier 303 and compound of interest 302 can be added directly to substantially liquid embolic composition 300 and take a final shape during the mixing process for example using a water-in-oil emulsion technique known in the art (not shown). In yet another embodiment, compound of interest 302 could also be first encapsulated within carrier 303 and formed into a final shape and be mixed with substantially liquid embolic composition 300 during the administration of the liquid embolic to the patient (not shown).

In one embodiment, the compound of interest 302 shown in FIG. 3A is a radiopaque agent. As shown in FIG. 3B, upon solidification in the target lumen and due to the presence of the radiopaque agent (i.e. compound of interest 302), substantially solid embolic composition 300' may be highly radiopaque. Substantially solid embolic composition 300' shown in FIG. 3C may be less radiopaque than substantially solid embolic composition 300' shown in FIG. 3B as result of dissolution and outbound diffusion of the radiopaque agent. FIG. 3D depicts the substantially solid embolic composition 300' after the radiopaque agent 302 has completely diffused out leaving behind only radiolucent embolic material 301 in vessel lumen 304.

In another embodiment, the compound of interest 302 shown in FIG. 3A is a therapeutic agent, such as an active pharmaceutical ingredient (API). Carrier 303 can dissolve or degrade releasing the therapeutic agent (i.e. compound of interest 302) to diffuse out of substantially solid embolic composition 300'. It is also possible for carrier 303 to diffuse out of the substantially solid embolic composition 300' carrying the therapeutic agent to its intended target site before releasing it (e.g. into a cancerous tumor—not shown). In this embodiment, said therapeutic agent or agents may include, but are not limited to anti-neoplastic drugs such as alkylating agents, antimetabolites, antibiotics, plant alkaloids and hormonal agents, anti-angiogenic compounds, and radioactive materials (e.g. yttrium 90), or other radiopharmaceuticals like radioactive iodine. Preferred therapeutic agents may include plant alkaloids such as paclitaxel or irinotecan, or anthrocycline antibiotics such as doxorubicin, tetracycline, idarubicin and mitomycin.

Figure 3E:
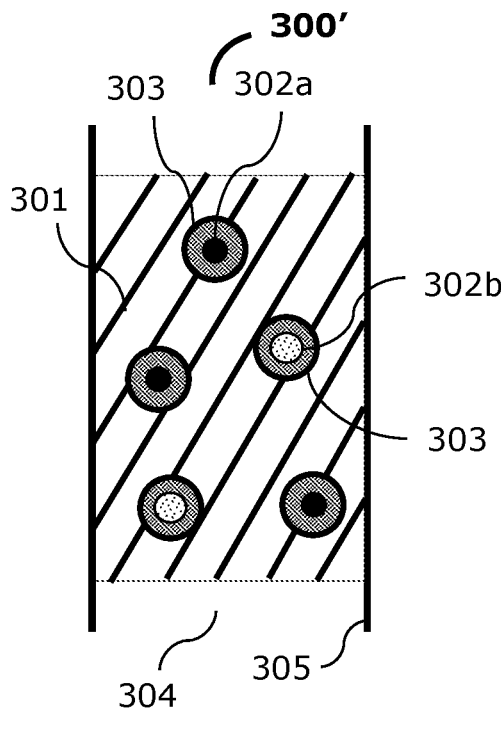
FIG. 3E depicts a longitudinal cross sectional view of a blood vessel embolized using a liquid embolic composition of the invention with multiple (different) compounds of interest in the same carrier dispersed within it.
Figure 3F:
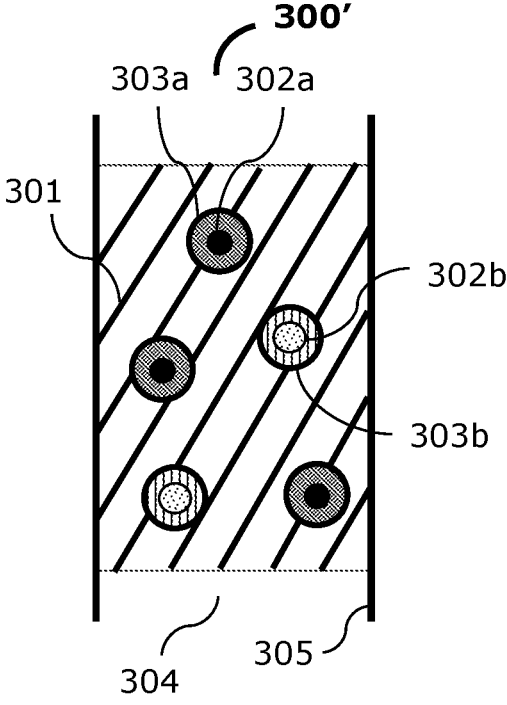
FIG. 3F depicts a longitudinal cross sectional view of a blood vessel embolized using a liquid embolic composition of the invention with multiple (different) compounds of interest in different carriers dispersed within it.

FIGS. 3E to 3F depicts a longitudinal cross sectional view of a blood vessel with lumen 304 and vessel walls 305. Specifically, FIG. 3E depicts an embodiment of the invention having multiple compounds of interest 302a and 302b each encapsulated within carriers 303 and dispersed within substantially solid embolic composition 300' shown embolizing lumen 304. The choice and ratio of compound of interest 302a to compound of interest 302b can be decided according to the desired clinical outcome. The relative concentration of compound of interest 302a to 302b, the choice of carrier 303, its size and chemical composition, and the permeability of substantially solid embolic composition 300' determine the rates of release of compounds of interest 302a and 302b from substantially solid embolic composition 300'. For example, in a scenario where compound of interest 302a and compound of interest 302b are of similar concentration, it is expected that both compounds of interest will likely be released at similar rates (not shown).

In one example of the embodiment shown in FIG. 3E, compound of interest 302a is a radiopaque agent and compound of interest 302b is a therapeutic agent, such as an active pharmaceutical ingredient (API). The concentration of the radiopaque agent and the therapeutic agent can be decided based on the desired radiopacity, the radiodensity of the radiopaque agent along with consideration of the desired therapeutic outcome and potency of the therapeutic agent. For example, the radiopaque agent and the therapeutic agent can be present in the substantially solid embolic composition 300' at a ratio of 2:1 (not shown).

FIG. 3F depicts an embodiment of the invention wherein compound of interest 302 is a combination of a compound of interest 302a and another compound of interest 302b each encapsulated within unique or different carriers 303a and 303b, respectively, and dispersed within substantially solid embolic composition 300'. In this scenario, the choice and concentration of the compounds of interest 302a and 302b, and the choice and size of corresponding carriers 303a and 303b can be decided according to the desired clinical outcome. For example, the composition of carriers 303a and 303b may be chosen based on the desired release profile for compound of interest 302a and the desired release profile for compound of interest 302b and their respective chemical compatibilities with the chosen carrier. For example, compound of interest 302a could be a hydrophilic molecule and compound of interest 302b could be a lipophilic molecule with each requiring compatible carriers 303a and 303b, respectively.

In yet another example of the embodiment of the invention shown in FIG. 3F, compound of interest 302a is a therapeutic agent and compound of interest 302b is a radiopaque agent, such as active pharmaceutical ingredient (API). Carriers 303a and 303b may each be fabricated of varying or different compositions in order to produce the desired release profile for each of the compounds of interest 302a and 302b. For example, it might be desirable to release the therapeutic agent over months or perhaps years and release the radiopaque agent over days, weeks or months. FIG. 3G depicts a graphical representation of the potential release kinetics of multiple compounds of interest (i.e. percentage release of each compound versus time) per the embodiment of the invention detailed in FIG. 3F. In this figure, the release curve shown is for an exemplary substantially solid embolic composition 300' wherein carrier 303a which encapsulates a therapeutic agent has a slower rate of dissolution and/or degradation compared to that of carrier 303b which encapsulates a radiopaque agent. This results in a slower release, outbound diffusion and/or dissipation of the radiopaque agent versus the therapeutic agent.

FIG. 3H depicts yet another embodiment of the invention which includes multiple compounds of interest 302a and 302b. In this embodiment, compound of interest 302a is encapsulated within carrier 303 and dispersed within substantially solid embolic composition 300' while compound of interest 302b is physically mixed with substantially solid embolic composition 300' without encapsulation in a carrier.

In one example of the above embodiment of the invention provided in FIG. 3H, compound of interest 302a is a radiopaque agent and compound of interest 302b is a therapeutic agent, such as an active pharmaceutical agent (API). The radiopaque agent is encapsulated within carrier 303 and dispersed within substantially solid embolic composition 300'. In this example, the therapeutic agent is directly dispersed within substantially solid embolic composition 300' and can be released into the blood stream and surrounding tissues (not shown) via diffusion while the release of the radiopaque agent is dependent on the dissolution, degradation and/or diffusion of carrier 303. The release of therapeutic agent, however, is also dependent on its saturated solubility in aqueous media in a similar mechanism as depicted in FIGS. 1A to 1D. The substantially solid embolic composition 300' of this example loses radiopacity and releases therapeutic agent over time although through two different mechanisms (not shown). Although obvious, the compounds of interest provided in this example embodiment could be reversed if desired. That is, the radiopaque agent could be dispersed within substantially solid composition 300' and the therapeutic agent could be encapsulated by carrier 303. In this instance, the radiopaque agent would be available for release via diffusion and the therapeutic agent would be available for release after carrier 303 degrades or dissolves.

In another example of the embodiment of the invention depicted in FIG. 3H, compound of interest 302a is a therapeutic agent, such as an active pharmaceutical agent (API) and compound of interest 302b is a radiopaque agent. The radiopaque agent may be selected or modified such that it does not substantially dissolve in aqueous media and therefore does not diffuse out of the substantially solid embolic composition 300' over time. The therapeutic agent, however, is encapsulated within carrier 303 and as such, the therapeutic agent is released from the substantially solid embolic composition 300' over time due to dissolution, degradation and/or diffusion of carrier 303 while radiopaque agent remains entrapped or sequestered within substantially solid embolic composition 300'.

FIG. 3I depicts the substantially solid embolic composition 300' of FIG. 3H comprising the radiopaque agent dispersed within the substantially solid embolic composition 300'. FIG. 3I also illustrates an absence of the therapeutic agent due to its complete release into the blood stream and surrounding tissue (not shown) following degradation and dissolution of carrier 303. The substantially solid embolic composition 300' of this example releases therapeutic agent over time while maintaining radiopacity permanently since the radiopaque agent selected for this example does not substantially dissolve in aqueous media (as previously detailed in the description of FIG. 3H).

In addition to physical encapsulation of compound of interest 302 in carrier 303 as depicted in FIG. 3A, compound of interest 302 can be chemically bound to the carrier 303 through chemical bonds (not shown). For example, the surface of carrier 303 can be chemically modified to be bound to compound of interest 302. In another embodiment compound of interest 302 can be co-polymerized with carrier 303 (not shown). In yet another embodiment, compound of interest 302 can be physically applied on the surface of carrier 303 for example in a core-shell composite (not shown).

In all embodiments of the invention provided herein, the permeability of the substantially solidified embolic composition, such as substantially solid embolic compositions 100' and 300', play a significant role in controlling the rate of the release of the compound of interest regardless of its method of encapsulation. This is due to the fact that a permeable embolic composition would allow for more biological fluids to enter the composition facilitating the dissolution and diffusion of the compound of interest or its carrier. The permeability of the embolic composition of this invention can be adjusted using techniques commonly known in the art such as the inclusion of pore forming agents within the composition. The pore forming agents can dissolve in biological fluids to create a desired porous structure. There are numerous well known, pore forming agents including, but not limited to synthetic or natural salts or sugars, sodium bicarbonate, ammonium bicarbonate, citric acid, baking powders, and mixtures thereof.

The rheology and injectability of the liquid embolic composition embodiments of this invention could be affected by the presence of the compound of interest. Therefore, it might be desirable to include other agents within the composition to adjust the physical properties of the embolic composition such as its viscosity to a desired level. These agents can include, but are not limited to thickeners, texturizers, gelation agents and stiffening agents such as polyethylene glycol, carboxymethyl cellulose, hydroxypropyl cellulose, alginate, chitosan, and mixtures thereof.

Herein are also provided methods of use for embodiments of liquid embolic compositions having controlled released. FIG. 4A provides a flow diagram detailing the use of a liquid embolic composition such as those shown in FIGS. 1A, 2A and 3A detailing the implantation of a liquid embolic composition have transient radiopacity. In this method, a typical interventional embolization procedure is proposed wherein a blood vessel to be treated is accessed using conventional catheter based devices, materials and interventional techniques well known in the art. If necessary, the catheter or microcatheter selected for delivery of the liquid embolic composition is primed with a solvent. This priming is typically done if the selected embolic composition polymerizes or precipitates or otherwise reacts with aqueous media or blood. For example, with EVOH/DMSO/tantalum based liquid embolic systems, the catheter or microcatheter is typically primed with DMSO, as premature contact of the liquid embolic with aqueous media or blood could trigger the precipitation reaction before it is desired. Once the catheter or microcatheter tip is positioned at or near the target vessels to be embolized using selective and subselective angiography, a syringe loaded with a liquid embolic composition of the invention could be attached to the proximal injection port of the catheter or microcatheter. Specifically in FIG. 4A, the embolic composition includes a compound of interest that is a radiopaque agent. Under real time fluoroscopic guidance, the liquid embolic composition would then be injected via the catheter or microcatheter to sufficiently embolize the target anatomy at the discretion of the physician operator. The liquid embolic composition would transform from a substantially liquid form or phase to a substantially solid form or phase embolizing or occluding the lumen or lumens of the targeted vessels. This solid embolic mass or implant effectively forms a cast within the vessel(s). Upon completion of the procedure (i.e. injection of liquid embolic material), the physician operator then gently retracts and removes the delivery catheter or microcatheter from the patient's body. Upon implantation and thereafter, the substantially solidified liquid embolic mass described in the method provided in FIG. 4A could then partially or fully dissipate its radiopacity to a level that reduces or eliminates post operative imaging artifacts and/or improves visualization in any subsequent diagnostic imaging and/or interventional medical procedures.

In an alternative embodiment, the method provided in FIG. 4B is identical to the method steps provided in FIG. 4A with the exception of adding a second compound of interest, namely a therapeutic agent or agents imparting controlled release. Each of the compounds of interest in the method provided in FIG. 4B could dissipate or elute from the embolic mass over time. Specifically, in this embodiment, the radiopacity of the substantially solidified cast or implant formed from a liquid embolic composition of the invention could maintain its radiopacity or alternatively partially or fully dissipate or elute its radiopacifier to reduce or eliminate post operative imaging artifacts and/or improves visualization in any subsequent diagnostic imaging and/or interventional medical procedures, while simultaneously releasing one or more therapeutic agents in a controlled manner It should be obvious to those skilled in the art and as previously described, the specific liquid embolic compositions which contain multiple compounds of interest could be designed using multiple permutations of differing compounds of interest (e.g. a radiopacifier only, a radiopacifier and an API or multiple APIs, an API or multiple APIs only, other radioactive materials or radiopharmaceuticals or combinations thereof) with their amounts/concentrations, elution kinetics and timing and the like tailored as desired for particular clinical applications or outcomes.

The invention claimed is:

1. An embolic composition capable of embolizing a blood vessel comprising:
   an embolic material and one or more compounds of interest,
   wherein the one or more compounds of interest is a combination of therapeutic agent and radiopaque agent that can diffuse out of the embolic composition and diminish the radiopacity of the embolic composition over time;

wherein all of the compounds of interest are entrapped or sequestered inside a biocompatible, degradable carrier; and
   wherein the therapeutic agent is released from the embolic composition in a controlled manner.

2. The embolic composition of claim 1 wherein the embolic composition undergoes a phase change from substantially liquid to substantially solid.

3. The embolic composition of claim 1 wherein the radiopacity of the embolic composition can diminish over time to an extent that the embolic composition does not present appreciable artifacts during any diagnostic imaging procedure.

4. The embolic composition of claim 1 wherein the biocompatible, degradable carriers that entrap or sequester the compounds of interest are microspheres, nano spheres, micelles, dendrimers, liposomes or lipid nanoparticles.

5. The embolic composition of claim 1 wherein the biocompatible, degradable carriers are capable of dissolution or degradation via hydrolysis or biological means.

6. The embolic composition of claim 1 wherein the compounds of interest are chemically bound to the embolic material via electrostatic bonding, covalent bonding, dipole-dipole attraction, ionic bonding, metallic bonding or hydrogen bonding.

7. The embolic composition of claim 6 wherein the chemical bonds can be broken by physical or biological mechanisms.

8. A method of use for a liquid embolic composition of the invention capable of embolizing a blood vessel comprising:
   accessing a blood vessel in a living organism via catheter-based devices and methods;
   inserting a delivery catheter at or near a target blood vessel to be embolized;
   injecting a substantially liquid embolic composition comprising an embolic material and one or more compounds of interest into the target blood vessel, wherein the one or more compounds of interest is a combination of therapeutic agent and radiopaque agent that can diffuse out of the embolic composition and diminish the radiopacity of the embolic composition over time, and wherein all of the compounds of interest are entrapped or sequestered inside a biocompatible, degradable carrier; and
   releasing the compounds of interest in a controlled manner from the substantially solid embolic composition into the blood vessel or surrounding tissues over time while maintaining permanent embolization of the target vessel.

9. The method of claim 8 wherein one or both of the radiopaque agent and the therapeutic agent is released in a controlled manner over a period of time.

10. The method of claim 8 wherein the substantially liquid embolic composition contains at least one compound of interest that is permanently entrapped within the substantially solidified embolic composition and at least one compound of interest that is capable of diffusing out of the substantially solidified embolic composition.

11. The method of claim 8 wherein the radiopaque agent is tantalum.

12. The method of claim 8 wherein the embolic material is ethylene vinyl alcohol.

13. The composition of claim 1 wherein the embolic material is ethylene vinyl alcohol and the radiopaque agent is tantalum.

\* \* \* \* \*